US005809693A

United States Patent [19]
Chet et al.

[11] Patent Number: 5,809,693
[45] Date of Patent: Sep. 22, 1998

[54] MICROBIAL ISOLATES PROMOTE PHYTOREMEDIATION

[75] Inventors: Ilan Chet, Nes Ziona, Israel; David Salt, Highland Park, N.J.; Michael Blaylock, Dayton, N.J.; Ilya Raskin, Manalapan, N.J.

[73] Assignee: Rutgers, The State University of New Jersey, New Brunswick, N.J.

[21] Appl. No.: 421,209

[22] Filed: Apr. 13, 1995

[51] Int. Cl.⁶ .............................. A01B 79/00; A01C 0/00; A01G 7/00; A01H 13/00; B01D 0/00; C20F 0/00; C20F 3/00; C20F 3/32; C07C 0/00; C07D 0/00; C07J 0/00; C07K 0/00; E02B 7/08; E02B 7/06; A01N 63/00; A01N 65/00; A61K 48/00; C07F 0/00; C07H 0/00

[52] U.S. Cl. .............................. 47/58; 47/1.4; 210/600; 210/601; 210/602; 435/262; 405/113; 405/117; 424/93.4; 424/93.46; 424/93.461; 424/93.462; 424/93.47

[58] Field of Search ............... 47/1.4, 58; 210/600, 210/601, 602; 435/262; 405/113, 117; 424/93.1, 93.2, 93.461, 93.462, 93.47, 93.48, 93.5, 93.7, 93.46, 93.4

[56] References Cited

U.S. PATENT DOCUMENTS

| | | | |
|---|---|---|---|
| 3,728,254 | 4/1973 | Carothers | 210/7 |
| 4,293,333 | 10/1981 | Drobot | 75/101 |
| 4,293,334 | 10/1981 | Drobot et al. | 75/101 |
| 4,310,990 | 1/1982 | Payne | 47/59 |
| 4,333,837 | 6/1982 | Plosz et al. | 210/602 |
| 4,372,080 | 2/1983 | Rushing | 47/57.6 |
| 4,678,582 | 7/1987 | Lavigne | 210/150 |
| 4,732,681 | 3/1988 | Galun et al. | 210/611 |
| 4,839,051 | 6/1989 | Higa | 210/602 |
| 4,849,008 | 7/1989 | Schroth et al. | 71/77 |
| 4,872,985 | 10/1989 | Dinges | 210/602 |
| 4,904,386 | 2/1990 | Kickuth | 210/602 |
| 4,959,084 | 9/1990 | Wolverton et al. | 210/601 |
| 4,975,105 | 12/1990 | Kremer et al. | 71/6 |
| 4,992,207 | 2/1991 | Darnall | 47/1.4 |
| 4,995,969 | 2/1991 | LaVigne | 210/150 |
| 5,000,852 | 3/1991 | Gel-Or | 210/602 |
| 5,061,490 | 10/1991 | Paau et al. | 424/93 |
| 5,099,049 | 3/1992 | Chamberlain | 556/148 |
| 5,100,455 | 3/1992 | Pinckard et al. | 71/9 |
| 5,106,504 | 4/1992 | Murray | 210/602 |
| 5,120,441 | 6/1992 | Jackson et al. | 210/602 |
| 5,121,708 | 6/1992 | Nuttle | 119/3 |
| 5,129,936 | 7/1992 | Wilson | 71/63 |
| 5,156,741 | 10/1992 | Morrison et al. | 210/602 |
| 5,159,135 | 10/1992 | Umbeck | 800/205 |
| 5,163,991 | 11/1992 | Kennedy et al. | 71/79 |
| 5,180,873 | 1/1993 | Jorgensen | 800/205 |
| 5,204,260 | 4/1993 | Ahmad et al. | 435/254 |
| 5,221,327 | 6/1993 | Rusin | 75/712 |
| 5,268,171 | 12/1993 | Polacco et al. | 424/93 R |
| 5,269,094 | 12/1993 | Wolverton et al. | 47/62 |
| 5,271,932 | 12/1993 | Savage et al. | 424/93 R |
| 5,288,296 | 2/1994 | McCabe et al. | 47/58 |

(List continued on next page.)

FOREIGN PATENT DOCUMENTS

| | | |
|---|---|---|
| 3406004 | 8/1985 | Germany . |
| 277905 | 4/1990 | Germany . |
| 3921336 | 10/1991 | Germany . |
| 4100758 | 7/1992 | Germany . |
| 4319992 | 12/1994 | Germany . |
| 57-000190 | 5/1982 | Japan . |
| 161297 | 6/1986 | Japan . |
| 647997 | 11/1989 | Japan . |
| 916438 | 4/1982 | U.S.S.R. . |
| 1411295 | 7/1988 | U.S.S.R. . |
| 9401367 | 1/1994 | WIPO . |
| WO 94/29226 | 12/1994 | WIPO ............................ C02F 3/32 |
| WO 9429466 | 12/1994 | WIPO . |

OTHER PUBLICATIONS

Baker et al., "The potential for heavy metal decontamination" Min. Env. Man. pp. 12–14, Sep., 1995.

Baker et al., "The potential for the use of metal–accumulating plants for the in situ decontamination of metal–polluted soils", Proc. EUROSOL Conf., Eur. Conf. on Integrated Res. Soil Sed. Protect. Remed., MECC Maastricht, the Netherlands, Sep., 1992.

Baker et al., "In situ decontamination of heavy metal polluted soils using crops of metal–accumulating plants—a feasibility study", In situ Bioreclamation : 600–605, 1991.

Baker et al., "Terrestrial higher plants which hyperaccumulate metallic elements—a review of their distribution, ecology, and phytochemistry", Biorecovery 1:81–126, 1989.

Bender et al., "Lead removal from contaminated water by a mixed microbial ecosystem", Wat. Sci. Tech. 21:1661–1664, 1989.

Berti et al., "Remediating soil Pb with green plants", presented at the Intl. Conf. of the Soc. for Env. Geochem. and Health, New Orleans, LA, Jul. 25–27, 1993 (pub'd Sep. 1993).

Bishop, "Pollution fighters hope a humble weed will help reclaim contaminated soil", Wall St. J., Feb. 29, 1996.

Boon et al., "Lead, cadmium, and zinc contamination of aspen garden soils and vegetation", Fert. Soils Plant Nutr. 116:775, 1992.

Cataldo et al., "Cadmium distribution and chemical fate in soybean plants", Plant Physiol. 68:835–839, 1981.

Chaney et al., "Potential use of metal hyperaccumulators", Mining Env. Management, pp. 9–11, Sep., 1995.

Checkai et al., "Effects of ionic and complexed metal concentrations on plant uptake of cadmium and micronutirient metals from solution", Plant and Soil, 99:335–345, 1987.

(List continued on next page.)

Primary Examiner—David T. Fox
Assistant Examiner—Kent L. Bell
Attorney, Agent, or Firm—Choate, Hall & Stewart; Sam Pasternack; Brenda H. Jarrell

[57] ABSTRACT

Methods and compositions or enhancing metal uptake of plants, such as members of the family Brassicaceae, comprise treating the roots, plants, seeds, and/or soil in which the plants are grown, with metal-uptake altering microorganisms, preferably of the bacterial genus Pseudomonas and Bacillus.

40 Claims, 3 Drawing Sheets

U.S. PATENT DOCUMENTS

| | | | |
|---|---|---|---|
| 5,292,456 | 3/1994 | Francis et al. ............................ | 252/628 |
| 5,320,663 | 6/1994 | Cunningham ............................ | 210/602 |
| 5,337,516 | 8/1994 | Hondulas .................................... | 47/65 |
| 5,364,451 | 11/1994 | Raskin et al. .............................. | 75/710 |
| 5,393,426 | 2/1995 | Raskin et al. ............................ | 210/602 |
| 5,422,268 | 6/1995 | Rusin .................................... | 435/262.5 |
| 5,436,384 | 7/1995 | Grant et al. ................................. | 588/1 |
| 5,458,747 | 10/1995 | Marks et al. ............................ | 204/130 |

OTHER PUBLICATIONS

Chigbo et al., "Uptake of arsenic, cadmium, lead and mercury from polluted waters by the water hyacinth *eichhornia crassipes*", Environ. Pollu. A:31–36, 1982.

Dierberg et al., "Removal of copper and lead using a thin–film technique" Aquatic Plants for Water Treatnebt and Resource Recovery, Magnolia Publishing (eds. Reddy and Smith), pp. 407–504, 1987.

Doushenkov, "Phytoremediation potential of crop plants", Supp. to Plant. Physiol 105:43, 1994 (Abstracts of papers from Ann. Mtg. of Ann. Soc. Plant Physiol., Portland, OR, Jul. 30, Aug. 3, 1994).

Evans et al., "Expression of the pea metallothionein–like gene $PsMT_A$ in *escherichia coli* and *arabidopsis thaliana* and analysis of trace metal ion accumulation: implications for $PsMT_A$ function", Plant. Mol. Bio. 20:1019–1028, 1992.

Haider et al., "Pollution control . . . ", UN Environ. Prog., 1984, pp. 627–634.

Halvorson et al., "The critical $Zn^{2+}$ concentration for corn and nonabsorption of chelated zinc", Soil Soc. A.M. J. 41:531–534, 1977.

Heaton et al., "Lead uptake by the water hyacinth", Aquatic plants for water treatment and resource recovery, Magnolia Publishing, Inc., pp. 471–485,_.

Heaton et al., "Lead uptake by *eichhornia crassipes*", Toxicol. Env. Chem. 11:125–135, 1986.

Heubert et al., "The effect of EDTA on cadmium and zinc uptake and toxicity in Lemna trisulco L", Arch. Environ, Contam. Toxicol. 22:313–318, 1992.

Jamil et al., "Biotransfer of metals to the insect *neochetina eichhornae* via aquatic plants", Arch. Evir. Contam. Toxicol. 22:459–63, 1992.

Kay et al., "Effects of heavy metals on water hyacinths (*eichhornia crassipes* (Mart.) Solms)", Aquatic Toxicol. 5:117–128, 1984.

Keefer et al., "Chemical composition of vegetables grown on an agricultural soil amended with sewage sludges", Biol. Abstr. 82:9330, 1986.

Lee et al., "Copper uptake by the water hyacinth", J. Environ. Sci. Health, A22:141–160, 1987.

M. "Dupont takes team approach to using plants for remediation", THe Bioremediation report, p. 4, Jan., 1995.

McGrath et al., "The potential for the use of metal–accumulationg plants for the in situ decontamination of metal–polluted soils", Soil Environ. _:673–676, 1993.

Misra et al., Heavy metal tolerant transgenic *brassica napus* and *nicotiana tabacum* L. plants:, Theor. Appl. Genet., 78:161–168, 1989.

Muramoto et al., "Removal of some heavy metals from polluted water by the water hyacinth (*eichhornia crassipes*)", Bull. Envir. Contam. Toxicol. 30:170–177, 1983.

Okieimen et al., "Removal of heavy ions from aqueous solution with melon (*citrullus vulgaris*) seed husks", Biological Wastes _:0269–7483, 1989.

Rauser, "Phytochelatins and related peptides", Plant Physiol. 109:1141–1149, 1995.

Reeves et al., "Abnormal accumulation of trace metals by plants", Mining Env. Management, pp. 4–7, Sep., 1995.

Stomp et al., "Genetic strategies for enhancing phytoremediation", Ann. NY Acad. Sci., 721:481–492. _.

Sunda et al., "Feedback interactions between zinc and phytoplankton in seawater", Limmol. Oceanog. 37:25–40, 1992.

Sunda et al., "The relationship between cupric ion activity and the toxicity of copper to phytoplankton", J. Marine Res. _:511–529, 1976.

Taiz et al., "Plant Physiology", Essential Elements, pp. 107–108, 1991.

Turnquist, "Nickel uptake by the water hyacinth", J. Environ. Sci. Health, A25:897–912, 1990.

Vallee et al., "Enzyme action: views derived from metalloenzyme studies", Chemistry in Britain 4:397–402, 1968.

Wills et al., "Absorption of $^{59}Fe$ by water hyacinths", Aquatic Plants for Water Treatment and Resource Recovery, Magnolia Publishing, pp. 471–485, _.

Wolverton, "Aquatic plants for wastewater treatment: an overview", Aqu. Plants Treat. Res. Recov. , Magnolia Publishing, 1987.

Banks et al., "Effects of plants and soil microflora on leaching of znc from mne failings", Chemosphere, 29:1691–9, 1994.

* Conley et al., "An assessment of the root zone method of wastewater treatment", J. Water. Poll. Control. Fed. 63:239–247, 1991.

Doushenkov et al., "Rhizofiltration: the use of plants to remove heavy metals from aqueous streams", Environ. Sci. Technol., 29:1239, 1995.

Müller et al., "Leaching of zinc from an industrial filter dust with Pencillium, Pseudomonas and Corynebacterium: citric acid is the leaching agent rather than amino acids", J. Indust. Microbiol., 14:208, 1995.

* Salt et al., "Phytoremediation: a novel strategy for the removal of toxic metals from the environment using plants", Bio/Technology, 13:468, 1995.

Weissenhorn et al., "Arbuscular mycorrhizal contribution to heavy metals uptake by maize (Zee mays L.) in pot culture with contaminated soil", Mycorrhiza, 5:245, May 12, 1995.

Barber et al., "The effect of micro–organisms on the absorption of manganese by plants", New. Phytol., 73:97–106, 1974.

Crowley, "Mechanisms of iron acquisition from siderophores by microorganisms and plants", Plant and Soil, 130:179–198, 1991.

Elad et al., "Possible role of competition for nutrients in biocontrol of pythium damping–off by bacteria", Ecology and Epidermiology, vol. 77, No. 2, 1987.

Elad et al., "Rhizosphere colonization by serratia marcescens for the control of sclerotium ROLFSII", Soil. Biol. Biochem., vol. 19, No. 6, pp. 747–751, 1987.

Raskin et al., Biocentration of heavy metals by plants, Current Opinion in Biotechnology, 5:285–290, 1994.

Jørgensen, "Removal of heavy metals from compost and soil by ecotechnological methods", Ecological Engineering, 2:89–100, Elsevier Science Publishers B.V., Amsterdam, 1993.

Barber et al.; The Effect of Micro–Organisms on the Absorption of Manganese by Plants; New Phytol. (1974) 73, 97–106.

Bar–Ness et al.; Short–Term Effects of Rhizosphere Microorganisms on Iron Uptake from Microbial Siderophores by Maize and Oat; Plant Physiol (Bethesda) 100(1) 1992 451–456 (Abstract Only).

MICROBIAL ISOLATES PROMOTE PHYTOREMEDIATION

BACKGROUND OF THE INVENTION

Agricultural growers and researchers have developed methods of improving root crop yield, and it has been known for many years that some soil microorganisms that are beneficial to plant growth may be added to the soil to either enhance production of plant hormones, produce antibiotics that kill harmful soil organisms, or aid in incorporation of inorganic mineral nutrients, such as iron and manganese, into the plant.

In a commonly used method, root crop production is enhanced, and root crop diseases, such as root rot, are inhibited by treating the seeds, seed pieces, or roots, or by inoculating the soil, with bacteria isolated from roots or tubers and selected for their ability to inhibit the growth of common plant pathogens. Such growth-promoting root and tuber-associated bacteria are subsequently introduced into the soil surrounding a root or tuber crop, usually at concentrations much higher than naturally present. The method is particularly useful for introducing such bacteria into soils where they are not naturally present.

Recently, researchers have developed methods of using crop plants to remove pollutants such as heavy metals from soils and waters. See, for example, U.S. Pat. No. 5,393,426 and Raskin et al., Current Opinion in Biotechnology, 5:285–290 (1994). These methods are, however, subject to the normal constraints imposed on conventional agronomic practices by bad weather, poor soil drainage, inadequate soil fertilization, and the like.

SUMMARY OF THE INVENTION

The present invention solves these problems and is based, in part, on our discovery that plant uptake of heavy metals can be altered (i.e. enhanced or inhibited) by the administration, directly to the soil/plant environment, of isolated microorganisms that are associated with plant roots. These microorganisms have the ability to tolerate heavy metals in their growth medium.

In one aspect, a method for altering uptake of a heavy metal by a plant includes contacting a plant with an isolated microorganism that is capable of altering heavy metal uptake of the plant, and then incubating the plant and isolated microorganism for a time and under conditions sufficient for the isolated microorganism to alter heavy metal uptake of the plant. It is preferred that the isolated microorganism is obtained from an environment of use that contains a concentration of at least one heavy metal. The isolated microorganisms are obtained from the environment of use by extracting microorganisms from a rhizosphere portion of the plant; exposing the extracted microorganisms to selective growth conditions such that only those microorganisms capable of growing in the presence of heavy metals will proliferate; and purifying the selected microorganisms. Preferred microorganisms for use in the present method include bacteria and fungi.

An additional method for altering heavy metal uptake of a plant includes obtaining a series of isolated microorganisms from a heavy metal-containing environment of use, preferably an environment that includes a rhizospheric portion of the plant. Next, one determines to what extent individual members of the isolated microorganisms alter heavy metal uptake of the plant. At least one member of the series of isolated microorganisms is chosen that is capable of altering heavy metal uptake by the plant and this member is reintroduced back into the environment of use. The environment of use may include a hydroponic environment.

A further embodiment of the invention is a composition for altering heavy metal uptake by a plant. The composition includes at least one isolated microorganism capable of altering heavy metal uptake of the plant in combination with an agronomically acceptable carrier. A preferred composition includes bacteria of the genus Pseudomonas or the genus Bacillus in a concentration from about $10^3$ cells/ml to about $10^{10}$ cells/ml in a carrier that may be a seed of the plant, a wettable powder, a dust, or granules. A method of using the composition to alter heavy metal uptake of a plant includes applying an effective amount of the composition to a plant seed prior to planting of the seed, applying an effective amount of the composition to soil where a plant seed is to be planted, or applying an effective amount of the composition to roots of the plant.

DETAILED DESCRIPTION OF THE INVENTION

The present invention pertains to methods of using isolated microorganisms selected from the rhizosphere of plants growing in environments containing amounts of heavy metals. Specifically, we have discovered that microorganisms may be isolated from soils contaminated with heavy metals, and when the isolated microorganisms are applied to the plant under appropriate conditions during phytoremediation, heavy metal uptake of the plant is altered.

The term "heavy metal" refers to soluble or insoluble metals. The term "soluble metals" preferably refers to soluble metal cationic or anionic species, which may be soluble in solution at environmentally relevant temperatures (e.g., greater than 0 degrees C. to less than about 45 degrees C.). "Insoluble metals" refers to metal ions that are substantially insoluble in solution at environmental relevant temperatures and also includes non-ionic, elemental forms of the metal. The present method is useful for enhancing phytoremediation of metals selected from the commonly known heavy metals and radioactive metals such as zinc, cadmium, chromium, lead, copper, silver, nickel, aluminum, manganese, arsenic, mercury and selenium, as well as radionuclides such as strontium, uranium, cesium, and others.

The term "alter" refers to the ability of the microorganisms to either increase or decrease the uptake of heavy metal by the plant, when compared to a plant lacking the population of isolated microorganisms.

The term "microorganisms" means prokaryotic or eukaryotic unicellular or multicellular organisms, and includes bacteria, actinomycetes, fungi, protozoans, slime molds and blue-green algae. The exact nature and type of microorganism is not intended to limit the methods of the invention. The term "isolated microorganism" means that the particular microorganism has been removed from its natural habitat, exposed to selective growth conditions, i.e., grown in the presence high concentrations of a heavy metal, and purified (see Example 1). Preferably, the term "isolated" refers to pure and mixed cultures of naturally occurring microorganisms that have been selected for their ability to grow and tolerate concentrations of heavy metals, as well as naturally occurring microorganisms that have been genetically manipulated so that they contain RNA or DNA polymers, portions of genomic nucleic acid, cDNA, synthetic nucleic acid and/or polypeptides encoded by these nucleic acids that: (i) are not associated with all of a nucleic acid or polypeptide with which it is associated in nature; or (ii) are linked to a nucleic acid, polypeptide, or other chemical moiety other than that to which it is linked in nature; or (iii) do not exist in nature. Methods of genetically manipulating bacteria are well known in the art (see, for example, Sambrook et al., *Molecular Cloning: A Laboratory Manual*, Cold Spring Harbor Press, Cold Spring Harbor, N.Y., 1989, incorporated herein by reference).

As but one example of the genetic manipulations useful in the present context, it is well known that many plants and microorganisms synthesize high-affinity metal transport systems (e.g., iron, zinc, copper, manganese) that utilize biosynthetic chelating agents called phytosiderophores and siderophores, respectively. Some microorganisms, such as *Escherichia coli* and *Streptomyces pilosus*, may actually use other siderophores in addition to their own (Crowley et al., Plant and Soil, 130: 179–198, 1991). Thus, plant DNA sequences encoding upon expression for one or more phytosiderophores can be introduced into isolated rhizosphere microorganisms in order to alter metal uptake of a plant.

The term "rhizosphere" is a term commonly used by persons having ordinary skill in the art and refers to that environment adjacent to the roots of a plant, regardless of whether the plant is growing in soil or in water.

The term "phytoremediation" refers to the practice of using plants to remove pollutants from the environment. The term "phytoremediation" is generic to methods that may be used for plants growing in soils ("phytoextraction": see U.S. Pat. No. 5,364,451, issued Nov. 15, 1994, incorporated herein by reference) or plants grown hydroponically in water ("rhizofiltration": see U.S. Pat. No. 5,393,426, issued Feb. 28, 1995, incorporated herein by reference).

The plants used in the preferred methods of the present invention may be either terrestrial plants or aquatic plants. The term "terrestrial plants" refers to photosynthetic plants that normally grow in soils or sediments, but that may be grown hydroponically. The soils or sediments can include a variety of soil types having wide ranges of water and organic matter content. Terrestrial plants can therefore include crop-related plants and/or plants associated with environments such as wetlands, as well as portions of such plants such as excised roots or shoots. "Aquatic plants" are those plants that spend their entire life cycle completely floating on, or submerged in, an aqueous solution, such as floating ferns (e.e., Azolla), duckweed (Lemna sp.), and water hyacinth (Eichhornia), as well as isolated plant cells or cell suspensions capable of metal uptake.

Plants particularly suitable for the present invention include turfgrasses and members of the family Brassicaceae as well as the common sunflower, *Helianthus annuus* L. Exemplary turfgrasses include Colonial bentgrass, Kentucky bluegrass, perennial ryegrass, creeping bentgrass, a variety of fescues and lovegrasses, Bermudagrass, Buffalograss, centipedegrass, switch grass, Japanese lawngrass and coastal panicgrass. Members of the Brassicaceae include *Brassica juncea* and *B. oleracea*. Other plants include spinach, sorghum, tobacco and corn. Plants may also include those plants that are selectively bred and/or genetically engineered.

Microorganisms useful in the present invention may be identified by first isolating a number of microbial strains from the vicinity of healthy roots, usually from the surfaces of such roots, by conventional microbiological methods (see, generally, Elad and Chet, 1987, "The Role of Competition for Nutrients in Biocontrol of Pythium damping off by bacteria", Phytopathology, 77: 190–195; Ordentlich et al., 1988, "Rhizospshere Colonization by *Serratia marcescens* for control of *Sclerotium rolfsii*, Soil. Biol. Biochem., 19: 747–751", each of which is incorporated herein by reference).

Microbial strains are directly selected for an ability to grow in high concentrations of heavy metals by successive rounds of supplementing microbial growth media with increasing concentrations of one or more heavy metals. Microbial colonies that are able to grow on heavy metal-contaminated media are reisolated on the same media and purified using conventional procedures. Microorganisms that have been subject to the selection pressure of heavy metal exposure are further selected for an ability to alter uptake of heavy metals by plants under particular plant growth conditions (see Examples 2–4).

Exemplary bacteria useful for the invention may be from the genus Bacillus and Pseudomonas. We have discovered strains of *Pseudomonas putida, Pseudomonas chlororaphis*, and *Bacillus thuringiensis* to be useful, although it will be appreciated that the specific strain of bacteria is not intended to limit the applicability of the method. In general, the methods of the present invention involve application of a single type of isolated microorganism, alone or in combination with one or more other isolated microorganisms, to seeds, seed pieces or roots of plants such as sunflower, Brassicas, potatoes, sugar beets, radishes and the like. Concentrations of at least about $10^3$ cells/ml can be used and preferably from about $10^5$ to about $10^9$ cells/ml can be used in combination with an agronomically acceptable carrier medium. A paste may be used to apply to the seeds at a concentration up to $10^{10}$ cells/ml. While it is preferred to apply the microorganisms directly to the seeds, or portions of plant prior to planting, the microorganisms can also be used to colonize soil in the area of planting prior to planting. In particular, they may be used to recolonize soil which has been fumigated or pasteurized.

The microorganisms may be utilized effectively in diverse formulations, including agronomically acceptable adjuvants and carriers normally employed for facilitating the dispersion of active ingredients for agricultural applications, recognizing as known fact that the dosage, formulation, mode of application, and other variables may affect its activity in any given application. Thus, the previously described exemplary pseudomonads and bacilli may be formulated as a suspension or dispersion, in aqueous or nonaqueous media, as a dust, as a wettable powder, as an emulsifiable concentrate, as a granule, or as any of several other known types of formulations, depending on the desired mode of application. These compositions may be applied as sprays, dust, or granules to the seeds, seed pieces, roots, plants, soil, or plant situs against which activity is desired. Microorganisms may also be added directly to the soil, in potting mixtures as well as directly to aqueous hydroponic systems.

In order to prepare compositions in the form of dust, granules, water dispersible powders, aqueous dispersions, or emulsions and dispersions in organic liquids, the carrier or diluent agent in such formulations may be a finely divided solid, an organic liquid, water, a wetting agent, a dispersing agent, or emulsifying agent, or any suitable combination of these. Generally, when liquids and wettable powders are prepared, a conditioning agent comprising one or more surface-active agents or surfactants is present in amounts sufficient to render a given composition containing the active material, the microorganism, dispersible in water or in oil.

Microorganisms are obtained as described herein and cultured by standard procedures. To convert the desired microorganism to a form which will facilitate the preparation of the following described compositions, a slurry is prepared which is then dried into a primary, agronomically acceptable carrier such as vermiculite, whereby the microorganism is adsorbed onto the carrier, becomes the concentrate for preparing the desired composition. If desired, the slurry can be used as the concentrate for fungal antagonist compositions.

The surface active agent used in the invention can be a wetting, dispersing, or emulsifying agent which will assist dispersion of the effective composition. The surface active agent or surfactant can include such anionic, cationic, and nonionic agents as have heretofore been generally employed in plant control compositions of similar types. Suitable surface-active agents are set forth, for example, in "Detergents and Emulsifiers", 1971 Annual by John W. McCutcheon, Inc.

In general, 1–10% by weight of the surface-active agent will be used in compositions of this invention and ordinarily the amount of surface-active agent will range from 1–5%, but may even be less than 1% by weight.

Additional surface-active agents can be added to formulations to increase the ratio of surfactants to active ingredients up to as high as 5:1 by weight. Such compositions may have a greater biological effectiveness than can be expected when the components are used separately. When used at higher ratios, it is preferred that the surfactant be present in the range of one-fifth to five parts surfactant for each one part of active agent. More specific formulations are disclosed in Examples 6 to 10, presented hereinafter.

EXAMPLES

Example 1

Selection and Identification of Microorganisms
I. Selection of Microorganisms
Phytoextraction: Plants growing in heavy metal contaminated soil were collected from sites in New Jersey (Jersey City and Trenton N.J.). The roots were cut and washed in 1 L tap water to remove the soil particles. The roots were then shaken in about 100 ml sterile water. Aseptic scrapings were also taken of the root surface and placed in about 2 ml sterile water. Aliquots of the sterile water containing the scrapings were diluted further for use in selection media, below.

Bacteria were selected on Pseudomonas agar F (mfg by Difco, Inc.) or soil extract agar and fungi were selected on Potato Dextrose agar (obtained from Difco, Inc.). All selection media were supplemented with 20 ug/ml of one or more of the following heavy metals: cadmium as $CdSO_4$, chromium (VI) as $K_2Cr_2O_7$ and lead as $Pb(NO_3)_2$.

After bacterial colonies were observed, they were picked using conventional sterile microbiological techniques and subject to further rounds of selection on Pseudomonas F agar supplemented with 1 ug/ml of one or more of the following heavy metals: cadmium as $CdSO_4$, lead as $Pb(NO_3)_2$, chromium (VI) as $K_2Cr_2O_7$, selenium as $Na_2SeO_4$, manganese as $MnCl_2$, nickel as $Ni(NO_3)_2$, and arsenic as $NaAsO_2$. Growing bacteria were reisolated to check the purity of the colony by re-streaking the bacteria onto the same media.

After fungal colonies were observed, colonies were purified by taking single spores from the colony or hyphal tips using conventional microbiological sterile technique and growing them on potato dextrose agar containing heavy metal, as above.

Rhizofiltration: Plants growing in heavy metal contaminated water were collected and the roots were cut and washed in 1 L tap water to remove the soil particles. The roots were then shaken in about 100 ml sterile water. Aseptic scrapings were also taken of the root surface and placed in about 2 ml sterile water. Aliquots of the sterile water containing the scrapings were diluted further for use in selection media, as described below.

Bacteria were selected on Pseudomonas agar F (mfg by Difco, Inc. address) or soil extract agar and fungi were selected on Potato Dextrose agar (obtained from Difco, Inc.). All selection media were supplemented with 20 ug/ml of one or more of the following heavy metals: cadmium as $CdSO_4$, chromium (VI) as $K_2Cr_2O_7$ and lead as $Pb(NO_3)_2$.

After bacterial colonies were observed, they were picked using conventional sterile microbiological techniques and subject to further rounds of selection on Pseudomonas F agar supplemented with 1 ug/ml of one or more of the following heavy metals: cadmium as $CdSO_4$, lead as $Pb(NO_3)_2$, chromium (VI) as $K_2Cr_2O_7$, selenium as $Na_2SeO_4$, manganese as $MnCl_2$, nickel as $Ni(NO_3)_2$, and arsenic as $NaAsO_2$. Growing bacteria were reisolated to check the purity of the colony by re-streaking the bacteria onto the same media.

After fungal colonies were observed, colonies were purified by taking single spores from the colony or hyphal tips using conventional microbiological sterile technique and growing them on potato dextrose agar containing heavy metal, as above.

II. Identification of Selected Microorganisms
Identification selected microorganisms was carried out by comparing the distribution of fatty acids using gas chromatography according to the methods of Sasser, M., "Identification of Bacteria Through Fatty Acid Analysis", pp. 199–204 in Methods in Phytobacteriology, (ed. Z. Klement, K. Rudolph, and D. Sands), 1990, Akademia Kiado Budapest, incorporated herein by reference.

Example 2

Growth of Selected Microorganisms and Application to Plant
Phytoextraction: Bacteria and fungi were grown in liquid Pseudomonas F medium and Potato Dextrose medium, respectively, in 250 ml Erlenmeyer flasks containing 100 ml medium with continuous shaking (about 135 rpm) for about 24 hours. Bacteria were collected by centrifugation at about 10,000 rpm, and fungi were collected by centrifugation at about 6,000 rpm. The respective pellets were washed twice by resuspension in 0.1M phosphate buffer (pH 7.0), followed by centrifugation.

Microbial water suspensions were added to phytoextraction systems by irrigation up to the field capacity of the soil. Suspensions contained $10^8$ bacteria/ml or $10^8$ CFU (colony forming units)/ml of fungi.

Rhizofiltration: Bacteria were grown in liquid Pseudomonas F medium and collected, as above. Bacterial suspensions (about $10^8$ bacteria/ml as a final concentration) were added to rhizofiltration systems by immersing hydroponically-grown roots in the suspension and then adding the rest of the suspension to the hydroponic solution itself.

Example 3

Greenhouse Screening for Altered Phytoextraction

Strains of selected microorganisms are grown on appropriate media (e.g., Pseudomonas liquid for bacteria; potato dextrose broth for fungi) for 48 hr, centrifuged, washed and resuspended. The pellet is diluted to give suspensions of approximately $10^8$–$10^9$ bacteria or CFU/ml. Several uniform Brassica juncea seelings are dipped for 5 min. in each suspension and planted in pots containing loamy sand field soil. Fresh weights of roots and shoots are taken from 4 week-old plants. These experiments are repeated three times with strains that alter heavy metal uptake.

Example 4

Screening for Altered Rhizofiltration

I. Methods

Alteration of Cadmium Uptake: Seeds of Brassica juncea were germinated and grown hydroponically with the roots growing in an aerated nutrient solution (a diluted and modified solution after Hoagland and Arnon, Univ. California Agricultural Experiment Station Circular 347–1938). The modified Hoagland's solution contained ammonium phosphate monobasic (0.25 mol m$^{-3}$); boric acid (12.5 mmol m$^{-3}$); calcium nitrate (0.7 mol m$^{-3}$); copper sulfate pentahydrate (0.075 mmol m$^{-3}$); ferric tartrate (4.75 mmol m$^{-3}$); magnesium sulfate anhydrous (0.5 mol m$^{-3}$); manganese chloride tetrahydrate (2.25 mmol m$^{-3}$); potassium nitrate (1.5 mol m$^{-3}$); and zinc sulfate heptahydrate (0.2 mmol m$^{-3}$). After about 1 week, bacterial or fungal suspensions were added to the roots of the seedlings, as described above, and plants allowed to grow for a further week. The 2 week old seedlings were then exposed to 1 micromolar cadmium containing $^{109}$Cd as a tracer, in modified Hoagland's solution for about 24 hours. Shoots and roots were harvested, washed and oven dried. Dried plant material was then ground and analyzed for Cd using a gamma counter with a solid NaI crystal scintillant.

Alteration of Lead Uptake: Seeds of Brassica juncea are germinated and grown hydroponically with the roots growing in an aerated Hoagland's nutrient solution as described above. After about 1 week, bacterial or fungal suspensions are added to the roots of the seedlings, as described above, and plants allowed to grow for a further week. Shoots and roots are harvested, washed and oven dried. Plants are then ashed at 500° C. and the solid material dissolved in a mixture of HCl and HNO$_3$. Lead is then measured in the solubilized plant material using Direct Current Plasma Optical Emission Spectroscopy (Fisons Model SS-7).

II. Results and Discussion

Figure 1:
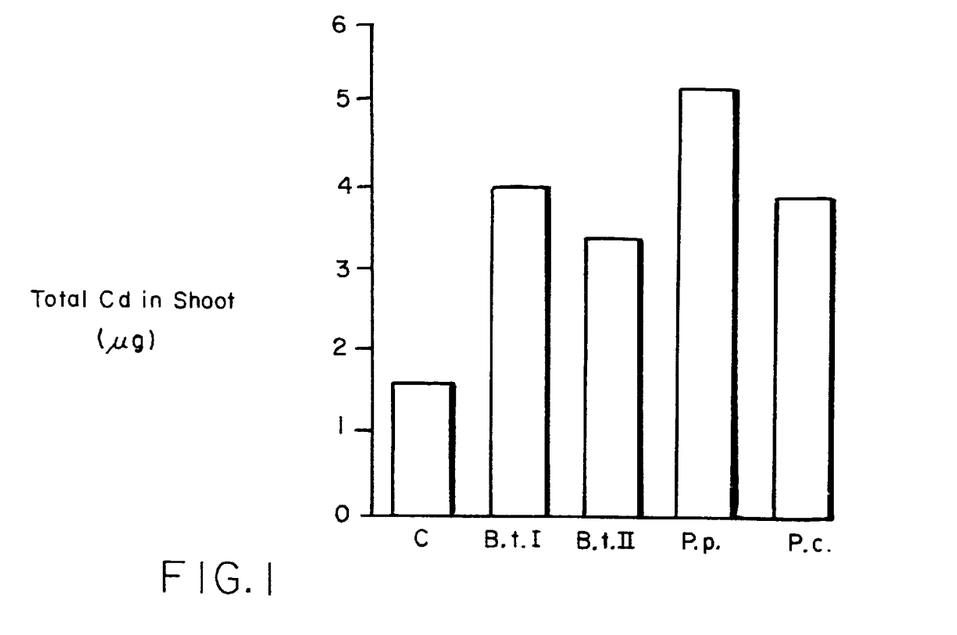
FIG. 1 is a graph illustrating total cadmium accumulation in shoots of 2-week old *B. juncea* seedlings grown hydroponically in the presence of isolated bacterial strains, previously selected from the rhizosphere of *B. juncea*. "B.t.I" denotes *Bacillus thuringiensis* strain I; "B.t.II" denotes *B. thuringiensis* strain II; "P.p." denotes *Pseudomonas putida*; "P.c." denotes *Pseudomonas chlororaphis*; and "C" denotes control treatment.
Figure 2:
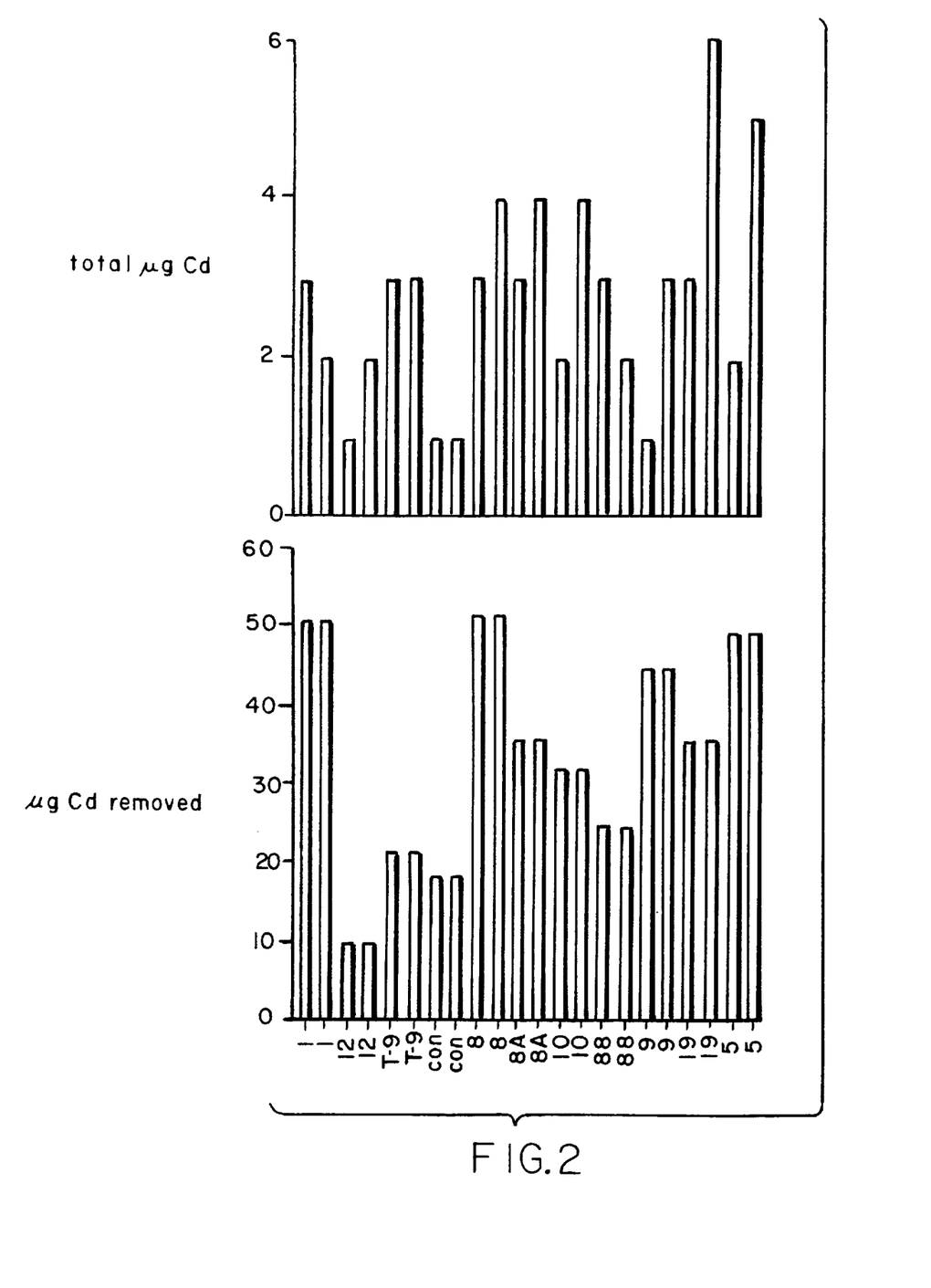
FIG. 2 is a graph illustrating total cadmium removal from solution (bottom graph) and total cadmium shoot concentration in shoots of 2-week old *B. juncea* seedlings grown hydroponically in the presence of isolated bacterial strains (X-axis), previously selected from the rhizosphere of *B. juncea*. The designation "con" refers to the control experiment. Strains "8", "10" and "19" refer to *Bacillus thuringiensis* strain I; *Pseudomonas putida*; and *B. thuringiensis* strain II, respectively.

Rhizofiltration: FIG. 1 illustrates the ability of Bacillus and Pseudomonas strains to enhance rhizofiltration of cadmium in B. juncea seedlings as compared to a control treatment in which the roots contained only endogenous rhizosphere bacteria and did not have isolated Bacillus and Pseudomonas strains added back to the roots. FIG. 2 is a series of graphs from another series of rhizofiltration experiments on B. juncea. Evidence of altered cadmium uptake is evidenced by the increased cadmium removal from solution (as compared to controls) and increased cadmium in the shoot (as compared to controls), when plotted against the isolated microbial strain applied to the plant. Most microbial isolates tended to increase accumulation of cadmium in plant shoots, when compared to the control treatments. Although variability in cadmium distribution within the plant shoot is to be expected, the results are not so variable as to mask the dramatic alteration in cadmium uptake due to some isolates.

Figure 3:
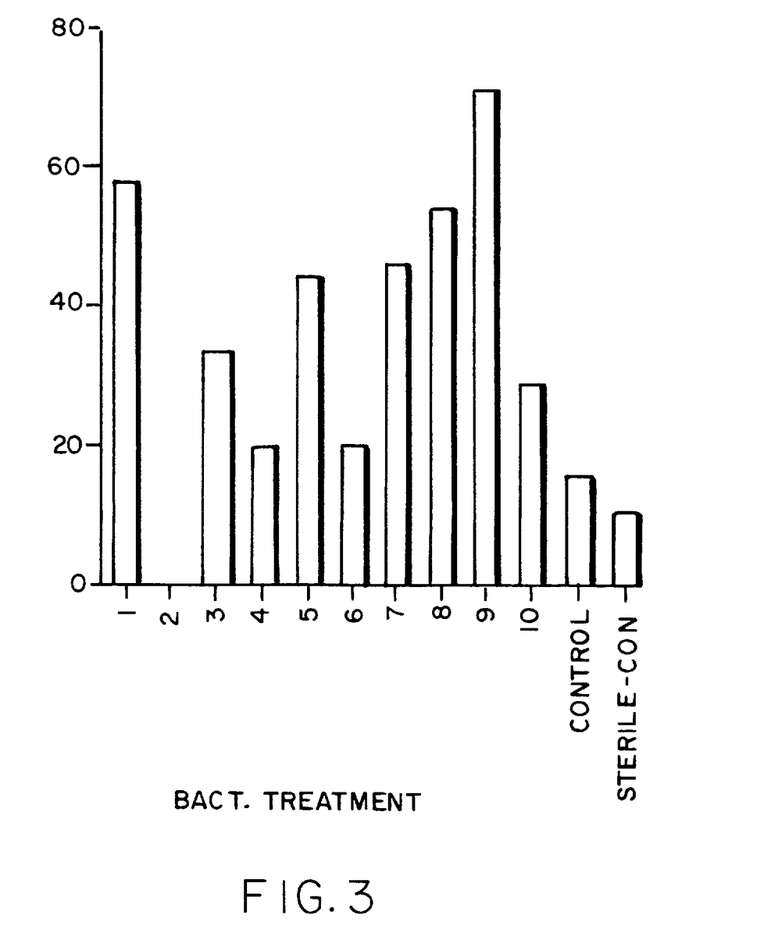
FIG. 3 illustrates the effect of isolated bacterial isolates on total lead accumulation during phytoextraction by *Brassica juncea*.
Figure 4:
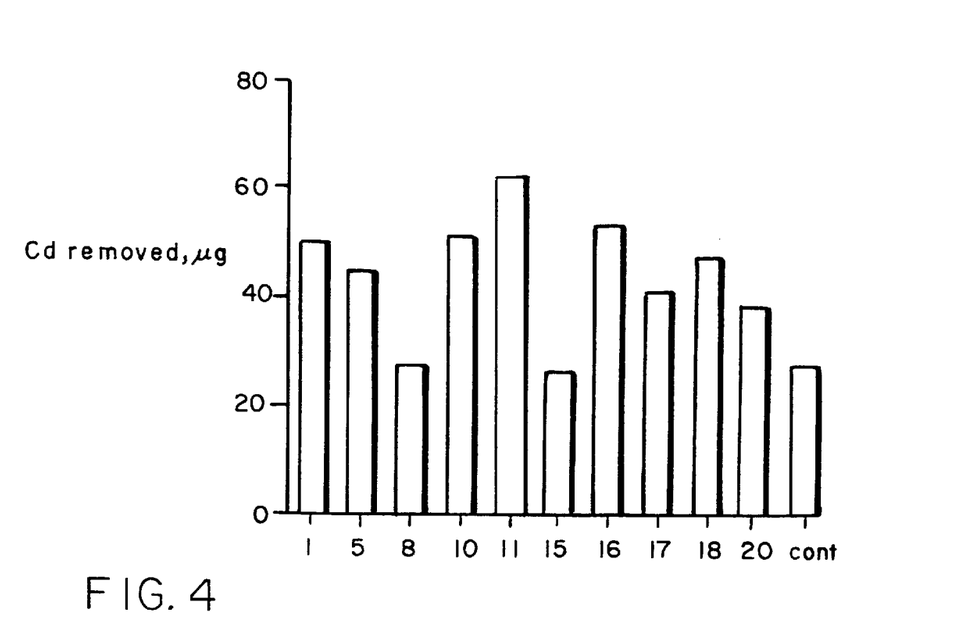
FIG. 4 illustrate the effect of isolated bacterial isolates on total cadmium accumulation during phytoextraction by *Brassica juncea*.

Phytoextraction: Bacteria and fungi were grown in liquid Pseudomonas F medium and Potato Dextrose medium, respectively, in 250 ml Erlenmeyer flasks containing 100 ml medium with continuous shaking (about 135 rpm), as above. Microbial water suspensions were added to laboratory-scale phytoextraction systems by irrigation up to the field capacity of the soil. Suspensions contained $10^8$ bacteria/ml or $10^8$ CFU (colony forming units)/ml of fungi. FIGS. 3 and 4 illustrate the effect of isolated bacterial isolates on total Brassica juncea accumulation during phytoextraction of lead and cadmium, respectively. Strain numbers 8 and 10 are B. thuringiensis Strain I and P. putida, respectively. The "sterile control" consisted of sterile soil. The "control" consisted of soil containing only endogenous rhizosphere bacteria and did not have isolated Bacillus and Pseudomonas strains added back to the soil. All isolates generally effected a net enhancement of metal removal from soil.

Example 5

Establishment of Microorganisms on Root Surfaces and in the Rhizospheres of Treated Plants Microbial strains (e.g., B. thuringiensis strain I) are extracted, selected and purified from freshly dug roots of, for example, Brassica juncea using methods described herein. Roots are dipped for 5 minutes in suspensions containing approximately $10^9$ CFU/ml of microbial strain. Roots are then placed on paper towels in the laboratory and sampled at various time intervals to determine the effect of air-drying on the survival of the inoculum. Laboratory temperature and relative humidity is about 24° C. and 20% RH during the air-drying period. Population determinations are made by removing root tissue from treated roots and placing them in 100 ml sterile distilled water. Serial water dilutions are subsequently made and plated on growth medium. One piece of root tissue from each of three roots is sampled at each time interval and three dilution plates are made from each peice. Plates are incubated for 24 hr at 28° C.

The ability of the microorganisms to survive on roots in field soil, or during hydroponic growth, is determined by previously described inoculation and sampling procedures. Generally, sampling of roots is made by excising one cm root sections from the tips and midsections of three roots per plant and washing them individually (along with soil particles in the case of phytoextraction experiments) with about 1 ml sterile distilled water. About 0.1 ml of these suspensions is plated on the appropriate medium. The population of microorganisms on roots of treated and non-treated roots may be followed over time using this procedure.

Example 6

Dusts

Dusts are dense powder compositions which are intended for application in dry form. Dusts are characterized by their free-flowing and rapid settling properties so that they are not readily windborne to areas where their presence is not desired. They contain primarily an active ingredient and a dense, free-flowing solid extender. Their performance is sometimes aided by the inclusion of a wetting agent, and convenience in manufacture frequently demands the inclusion of an inert absorptive grinding aid.

The wettable powder as described above can also be used in the preparation of dusts. While such wettable powders can be used directly in dust form, it is more advantageous to dilute them by blending with the dense dust diluent. In this manner, dispersing agents, corrosion inhibitors, and antifoam agents may also be used as components of a dust. Thus, the dust compositions of this invention can comprise from about 0.5 to 20.0 weight percent active ingredient, 5 to 25 weight percent filler, 0 to 1.0 weight percent wetting agent and from about 30 to 90 weight percent dense, free-flowing extender, as these terms are used herein. Such dust formulations can contain, in addition, minor amounts of dispersants, corrosion inhibitors, and antifoam agents derived from the wettable powders used to make the dust.

Example 7

Wettable Powders

Wettable powders are water-dispersible compositions containing the active material, an inert solid extender, and one or more surfactants to provide rapid wetting and to prevent heavy flocculations when suspended in water. The inert extenders which are preferred for use in the wettable powders of this invention containing the 25 active compounds are of mineral origin.

Extenders suitable for the wettable powder formulations of this invention are the natural clays, diatomaceous earth and synthetic mineral fillers derived from silica and silicate. Most preferred fillers for this invention are kaolinites, attapulgite clay, montmorillonite clays, synthetic silica, synthetic magnesium silicate and calcium sulfate dihydrate.

Among the more preferred surfactants are the non-ionic and anionic types. They are most suitable for the preparation of dry, wettable products of this invention and dispersants. Occasionally, a liquid, nonionic compound which is primarily an emulsifier, may serve as both wetter and dispersant.

Most preferred wetting agents are alkylbenzene and alkylnapthalene sulfonates, sulfated fatty alcohols, amines or acid amides, long chain esters of sodium isothionate, esters of sodium sulfosuccinate, sulfated or sulfonated vegetable oils, and ditertiary acetylenic glycols. Preferred dispersants are methyl cellulose, polyvinyl alcohol, lignin sulfonates, polymeric alkylnapthalene sulfonates, sodium naphthalene sulfonates, polymethylene bisnapthalene sulfonate and sodium-N-methyl-N-(long chain acid) taurates.

Wetting and dispersing agents in these preferred wettable powder compositions of the invention are usually present at concentrations of from about 0.5 weight percent to 5 weight percent. The inert extender then completes the formulation. Where needed, 0.1 weight percent of the extender may be replaced by a corrosion inhibitor or an antifoaming agent or both.

Thus, wettable powder formulations of the invention will contain from about 25 to 90 weight percent active material, from 0.5 to 2.0 percent wetting agent, from 0.25 to 5.0 weight percent dispersant, and from 9.25 to 74.25 weight percent inert extender, as these terms are described above.

When the wettable powder contains a corrosion inhibitor or an antifoaming agent or both, the corrosion inhibitor should not exceed about 1 percent of the composition, and the antifoaming agent should not exceed about 0.5 percent by weight of the composition, both replacing equivalent amounts of the inert extender.

Example 9

Emulsifiable Oils

Emulsifiable oils are usually solutions or suspensions of active material in nonwater miscible solvents together with a surfactant and/or emulsifier. For compositions of this invention, emulsifiable oil compositions can be made by mixing the active ingredient with an organic solvent and surfactant. Suitable surfactants are those ionic or nonionic agents known to the art as emulsifying agents.

Emulsifying agents most suitable for the emulsifiable oil compositions of this invention are long chain alkyl or mercaptan polyethoxy alcohols, alkylaryl polyethoxy alcohols, sorbitan fatty acid esters, polyoxyethylene ethers with sorbitan fatty acid esters, polyethylene glycol esters with fatty rosin acids, fatty alkylol amide condensates, calcium and amine salts of fatty alcohol sulfates, oil soluble petroleum sulfonates, or preferably mixtures of these emulsifying agents. Such emulsifying agents should compromise from about 1 to 10 weight percent of the total composition. As described above, however, up to 5 parts of emulsifying agent for each part of active ingredient can be used.

Thus, emulsifiable oil compositions of the present invention can consist of from about 10 to 50 weight percent active ingredients, about 40 to 82 percent solvents, and about 1 to 10 weight percent emulsifies, as these terms are defined and used above.

Example 10

Granules

Granules are physically stable, particulate compositions containing mycelium, sclerotia, spores, or other microorganisms which adhere to, or are distributed through, a basic matrix of a coherent, inert carrier with microscopic dimensions. In order to aid leaching of the active ingredient from the granule, a surfactant can be present. The inert carrier is preferably of mineral origin, and suitable carriers are natural clays, some pyrophyllites and vermiculite. Suitable wetting agents can be anionic or nonionic.

For the granule composition of this invention, most suitable carriers are of two types. The first are porous, absorptive pre-formed granules, such as preformed and screened granular attapulgite or heat expanded granular, screened vermiculite. On either of these, a suspension of the active agent can be sprayed and will be absorbed at concentrations up to 25 weight percent of the total weight. The second type are initially powdered kaolin clays, hydrated attapulgite or bentonite clays in the form of sodium, calcium or magnesium bentonites. Water-soluble salts such as sodium salts may also be present to aid in the disintegration of the granules in the presence of moisture. These ingredients are blended with the active components to give mixtures that are granulated, followed by drying to yield formulations with the active component distributed uniformly throughout the mass. Such granules can also be made with 25 to 30 weight percent active component but more frequently a concentration of about 10 weight percent is desired for optimum distribution. The granular compositions of this invention are believed to be most useful in a size range of 15–30 mesh.

The most suitable wetting agents for the granular compositions of this invention depend upon the type of granule used. When pre-formed granules are sprayed with active material in liquid form, the most suitable wetting agents are nonionic, liquid wetters miscible with the solvent. These are more generally known in the art as emulsifiers and compromise alkyl-aryl polyether alcohols, alkyl polyether alcohols, polyoxyethylene sorbitan fatty acid esters, polyethylene glycol esters with fatty or rosin acids, fatty alkylol amide concentrates, oil soluble petroleum or vegetable oil sulfonates, of mixtures of these. Such agents will usually compromise up to about 5 weight percent of the total composition.

When the active ingredient is first mixed with a powdered carrier and subsequently granulated, liquid non-ionic wetters can still be used, but it is usually preferable to incorporate at the mixing stage, one of the solid, powdered anionic wetting agents such as those previously listed for the wettable powders. Such agents should compromise about 0 to 2 weight percent of the total composition.

Thus, the preferred granular formulations of this invention compromise about 5 to 30 weight percent active material, about 0 to 5 weight percent wetting agent, and about 65 to 90 percent inert mineral carrier, as these terms are used herein.

EQUIVALENTS

Those skilled in the art will recognize, or will be able to ascertain using no more than routine experimentation, numerous equivalents to the specific products and processes described herein. Such equivalents are considered to be within the scope of the invention and are intended to be covered by the following claims.

We claim:

1. A method for increasing accumulation of a metal by a plant, the method comprising:
   selecting at least one isolated bacterial microorganism that is characterized by an ability to increase the availability of at least one non-essential metal to the plant;
   introducing into the rhizosphere of a plant, which plant is characterized by an ability to accumulate an amount of at least one non-essential metal from an environment contaminated with the at least one non-essential metal, the at least one selected bacterial microorganism that is characterized by an ability to increase availability of the at least one non-essential metal to the plant; and
   culturing the plant and the at least one isolated bacterial microorganism in an environment contaminated with the at least one non-essential metal, the culturing being performed for a time and under conditions sufficient for the isolated bacterial microorganism to increase availability of the at least one non-essential metal to the plant so that the plant accumulates a larger amount of the at least one non-essential metal in the presence of the at least one bacterial microorganism than the plant would accumulate in the absence of the at least one bacterial microorganism.

2. The method of claim 1, wherein the step of selecting comprises selecting at least one bacterial microorganism that is characterized by its survival when growing under conditions of selection pressure, the selection pressure comprising a higher than ambient concentration of the at least one non-essential metal, and wherein the step of introducing comprises introducing into the rhizosphere of the plant at least one bacterial microorganism that has been selected by its survival when growing under conditions of selection pressure, the selection pressure comprising a higher than ambient concentration of the at least one non-essential metal.

3. The method of claim 2, wherein the step of culturing comprises:
   introducing the plant and the at least one bacterial microorganism into a contaminated environment containing a concentration of the at least one non-essential metal that has been determined to be environmentally hazardous;
   allowing the plant to grow in the contaminated environment in the presence of the at least one bacterial microorganism, whereby bioavailability of the at least one heavy metal is increased by the at least one bacterial microorganism and the plant accumulates more metal than it would in the absence of the at least one bacterial microorganism.

4. A method for increasing accumulation of a non-essential metal by a plant, the method comprising:
   identifying a first plant growing in a first environment that includes at least one non-essential metal;
   extracting bacterial microorganisms from the rhizosphere of the first plant;
   progressively culturing the extracted bacterial microorganisms under conditions of increasing selection pressure comprising higher concentrations of the at least one non-essential metal;
   selecting the bacterial microorganisms that survive the conditions of increased selection pressure;
   multiplying those selected bacterial microorganisms that survive the conditions of increasing selection pressure;
   introducing the multiplied selected bacterial microorganisms into the rhizosphere of a second plant, which second plant has a natural ability to accumulate an amount of the at least one non-essential metal;
   culturing the multiplied selected bacterial microorganisms with the second plant in a second environment that contains the at least one non-essential metal, the second environment being either different from or the same as the first environment, whereby the second plant accumulates a larger amount of the at least one non-essential metal from the second environment than it would in the absence of the selected bacterial microorganisms.

5. The method of claim 3, wherein the step of culturing comprises culturing in a soil environment.

6. The method of claim 3, wherein the step of culturing comprises culturing in an aquatic environment.

7. A method for increasing accumulation of a metal by a plant, the method comprising:
   selecting at least one isolated bacterial microorganism, wherein the at least one selected microorganism is a member of a bacterial genus selected from the group consisting of Pseudomonas and Bacillus, that is characterized by an ability to increase the availibility of at least one non-essential metal to the plant;
   introducing into the rhizosphere of a plant, which plant is characterized by an ability to accumulate an amount of at least one non-essential metal from an environment contaminated with the at least one non-essential metal, the at least one selected bacterial microorganism that is characterized by an ability to increase availability of the at least one non-essential metal to the plant; and culturing the plant and the at least one selected bacterial microorganism in an environment contaminated with the at least one non-essential metal, the culturing being performed for a time and under conditions sufficient for the selected bacterial microorganism to increase availability of the at least one non-essential metal to the plant so that the plant accumulates a larger amount of the at least one non-essential metal in the presence of the at least one bacterial microorganism than the plant would accumulate in the absence of the at least one bacterial microorganism.

8. A method for increasing metal accumulation by a plant so that harvest of the plant would reduce the amount of metal in the environment in which the plant was growing, the method comprising steps of:

identifying an environment containing a concentration of at least one non-essential metal, the concentration being one that has been determined to be dangerous to humans;

removing at least a portion of the root system of at least one first plant growing in the environment;

sampling the rhizosphere of the removed root system of the at least one first plant to obtain bacterial microorganisms growing in the rhizosphere;

selecting, by a process of culturing the bacterial microorganisms in the rhizosphere of at least one second plant, those bacterial microorganisms that increase accumulation of the non-essential metal by the second plant;

isolating and multiplying the selected bacterial microorganisms;

re-introducing the isolated and multiplied selected bacterial microorganisms into the environment so that at least one bacterial microorganism is introduced into the rhizosphere of at least one crop plant growing in the environment; and growing the at least one selected bacterial microorganism in the rhizosphere of the at least one crop plant under conditions and for a time sufficient for the at least one bacterial microorganism to increase accumulation of the at least one non-essential metal by the at least one crop plant.

9. The method of claim 8, wherein the step of sampling comprises:

extracting bacterial microorganisms from the rhizosphere of the removed root system;

culturing the extracted bacterial microorganisms under selective growth conditions comprising increasing levels of a heavy metal such that only certain bacterial microorganisms survive; and isolating and multiplying the certain bacterial microorganisms.

10. A method of increasing metal accumulation by a plant, the method comprising steps of:

selecting at least one isolated bacterial microorganism capable of altering heavy metal uptake of the plant;

applying to a seed of a plant an effective amount of a composition, where the composition includes the at least one selected bacterial microorganism capable of altering heavy metal uptake of the plant in combination with an agronomically acceptable carrier;

planting the seed in an environment containing at least one non-essential metal; and growing a plant from the seed under conditions sufficient for the at least one selected bacterial microorganism to proliferate in the rhizosphere of the plant and increase accumulation of the at least one non-essential metal by the plant to a higher level than would be accumulated in the absence of the composition.

11. A method of increasing metal accumulation by a plant, the method comprising steps of:

selecting at least one isolated bacterial microorganism capable of altering heavy metal uptake of the plant;

applying to a soil that includes the at least one non-essential metal an effective amount of a composition, where the composition includes the at least one selected bacterial microorganism;

planting in the soil a seed of a plant that is capable of accumulating the at least one non-essential metal; and growing the plant from the seed under conditions sufficient for the at least one selected bacterial microorganism to proliferate in the rhizosphere of the plant and increase metal accumulation by that plant to a level higher than it would be in the absence of the composition.

12. A method of increasing metal accumulation by a plant, the method comprising:

selecting at least one isolated bacterial microorganism capable of altering heavy metal uptake of the plant;

applying to roots of a plant that is characterized by an ability to accumulate at least one non-essential metal an effective amount of a composition, where the composition includes the at least one selected bacterial microorganism capable of altering heavy metal uptake of the plant in combination with an agronomically acceptable carrier; and growing at least the roots of the plant in an environment containing the at least one non-essential metal under conditions sufficient for the at least one selected bacterial microorganism to proliferate in the rhizosphere of the plant and increase metal accumulation by the plant to a level higher than it would be in the absence of the composition.

13. The method of claim 12, wherein the step of growing comprises growing the roots of the plant in an aquatic environment.

14. A method of increasing metal uptake by a plant, the method comprising steps of:

providing at least one isolated bacterial microorganism that synthesizes a biosynthetic chelating agent;

subjecting the isolated microorganism to selection conditions consisting of elevated concentrations of one or more metal and selecting those that survive;

introducing the at least one selected bacterial microorganism into the rhizosphere of a plant, the introduction being performed in an environment that contains a metal that is not essential for plant growth;

maintaining the plant and bacterial microorganism together in the environment under appropriate conditions and for a sufficient time so that the plant accumulates an amount of the non-essential metal that is larger than the amount that the plant would accumulate if grown under the same conditions and for the same amount of time but in the absence of the selected bacterial microorganism.

15. The method of claim 14 wherein the step of introducing comprises introducing the at least one isolated bacterial microorganism into the rhizosphere of a plant, the introduction being performed in an environment that contains at least one non-essential metal selected from the group consisting of cadmium, chromium, lead, copper, silver, nickel, aluminum, arsenic, mercury, and selenium.

16. The method of claim 14 wherein the step of introducing comprises introducing the at least one isolated bacterial microorganism into the rhizosphere of a plant, the introduction being performed in an environment that contains at least one non-essential metal that is a radionuclide selected from the group consisting of strontium, uranium, and cesium.

17. The method of claim 14 wherein the step of introducing comprises introducing the at least one bacterial microorganism into the rhizosphere of a plant, the introduction being performed in an environment that contains at least one non-essential metal selected from the group consisting of cadmium and lead.

18. A method of increasing metal uptake by a plant, the method comprising steps of:
selecting at least one isolated bacterial microorganism that synthesizes a biosynthetic chelating agent, which microoganism is selected from the group consisting of Pseudomonas and Bacillus;
introducing the at least one microorganism into the rhizosphere of a plant, the introduction being performed in an environment that contains a metal that is not essential for plant growth;
maintaining the plant and bacterial microorganism together in the environment under appropriate conditions and for a sufficient time so that the plant accumulates an amount of the non-essential metal that is larger than the amount that the plant would accumulate if grown under the same conditions and for the same amount of time but in the absence of the bacterial microorganism.

19. A method of increasing metal uptake by a plant, the method comprising steps of:
selecting at least one isolated bacterial microorganism, that synthesizes a biosynthetic chelating agent, which microorganism is selected from the group consisting of *Pseudomonas putida* and *Pseudomonas chlororaphis* bacteria;
introducing the at least one microorganism into the rhizosphere of a plant, the introduction being performed in an environment that contains a metal that is not essential for plant growth;
maintaining the plant and bacterial microorganism together in the environment under appropriate conditions and for a sufficient time so that the plant accumulates an amount of the non-essential metal that is larger than the amount that the plant would accumulate if grown under the same conditions and for the same amount of time but in the absence of the bacterial microorganism.

20. A method of increasing metal uptake by a plant, the method comprising steps of:
selecting at least one isolated bacterial microorganism, that synthesizes a biosynthetic chelating agent, which microorganism comprises *Bacillus thuringiensis* bacteria;
introducing the at least one microorganism into the rhizosphere of a plant, the introduction being performed in an environment that contains a metal that is not essential for plant growth;
maintaining the plant and bacterial microorganism together in the environment under appropriate conditions and for a sufficient time so that the plant accumulates an amount of the non-essential metal that is larger than the amount that the plant would accumulate if grown under the same conditions and for the same amount of time but in the absence of the bacterial microorganism.

21. The method of claim 14 wherein the step of introducing comprises introducing the at least one bacterial microorganism into the rhizosphere of a turfgrass plant.

22. The method of claim 14 wherein the step of introducing comprises introducing the at least one bacterial microorganism into the rhizosphere of a turfgrass plant selected from the group consisting of Colonial bentgrass, Kentucky bluegrass, perennial ryegrass, creeping bentgrass, fecus, lovegrass, Bermudagrass, Buffalograss, centipedegrass, switch grass, Japanese lawngrass, and coastal panicgrass.

23. The method of claim 14 wherein the step of introducing comprises introducing the at least one bacterial microorganism into the rhizosphere of a plant that is a Brassicaceae family member selected from the group consisting of *Brassica juncea* and *Brassica oleracea*.

24. The method of claim 14 wherein the step of introducing comprises introducing the at least one bacterial microorganism into the rhizosphere of a plant selected from the group consisting of spinach, sorghum, tobacco, and corn.

25. The method of claim 14 wherein the step of providing comprises isolating the at least one bacterial microorganism by a process including steps of:
identifying a first environment containing at least one first non-essential metal;
removing bacterial microorganisms from the first metal-containing environment;
growing the removed bacterial microorganisms in the presence of at least one second non-essential metal, the same as or different from the at least one first non-essential metal, so that only bacterial microorganisms that tolerate the at least one second non-essential metal survive; and
isolating surviving bacterial microorganisms.

26. The method of claim 25 wherein:
the step of identifying comprises identifying a first environment containing at least one first non-essential metal and also containing plant life; and
the step of removing bacterial microorganisms from the first metal-containing environment comprises removing at least roots of the plant life from the first environment, so that bacterial microorganisms associated with the roots are thereby removed; and
the step of growing comprises growing bacterial microorganisms that were associated with the plant life roots.

27. The method of claim 1 wherein the step of introducing comprises introducing the at least one isolated bacterial microorganism into the rhizosphere of a crop plant.

28. The method of claim 4 wherein the step of introducing comprises introducing the multiplied bacterial microorganisms into the rhizosphere of a second plant, which second plant is a crop plant.

29. The method of claim 10 wherein the step of applying comprises applying an effective amount of the composition, where the composition includes at least one isolated bacterial microorganism capable of altering heavy metal uptake of the plant in combination with an agronomically acceptable carrier, to a seed of a crop plant.

30. The method of claim 11 wherein the step of planting comprises planting in the soil a seed of a crop plant that is capable of accumulating the at least one non-essential metal.

31. The method of claim 14 wherein the step of introducing comprises introducing the bacterial microorganisms into a rhizosphere of a crop plant.

32. A method comprising steps of:

selecting at least one isolated bacterial microorganism characterized by an ability, when cultured in the rhizosphere of the plant in an environment containing at least one non-essential metal, to increase the availability of the at least one non-essential metal to the plant within the environment;

providing a crop plant that is capable of accumulating an amount of at least one metal that is not essential to plant growth;

introducing into the rhizosphere of the crop plant at least one isolated bacterial microorganism characterized by an ability, when cultured in the rhizosphere of the plant in an environment containing the at least one non-essential metal, to increase availability of the at least one non-essential metal to the plant within the environment; and culturing the plant and bacterial microorganism in the metal-containing environment so that the plant accumulates a larger amount of the at least one non-essential metal than the plant would accumulate in the absence of the at least one bacterial microorganism.

33. The method of claim 32 wherein the step of selecting comprises selecting at least one isolated bacterial microorganism characterized by an ability to increase availability of a non-essential metal selected from the group consisting of cadmium and lead; and wherein the step of providing comprises providing a crop plant that is capable of accumulating an amount of a non-essential metal selected from the group consisting of cadmium and lead.

34. The method of claim 33 wherein:

the step of selecting comprises selecting at least one isolated bacterial microorganism characterized by an ability, when cultured in the rhizosphere of the plant in an environment containing cadmium, to increase availability of the cadmium to the plant sufficiently so that the plant accumulates at least about two fold more cadmium in the presence of the at least one isolated bacterial microorganism than it would in the absence of the at least one bacterial microorganism;

the step of providing comprises providing a crop plant that is capable of accumulating an amount of cadmium; and the step of introducing comprises introducing into the rhizosphere of the crop plant at least one isolated bacterial microorganism characterized by an ability, when cultured in the rhizosphere of the plant in an environment containing cadmium, to increase availability of the cadmium to the plant sufficiently so that the plant accumulates at least about two fold more cadmium in the presence of the at least one isolated bacterial microorganism than it would in the absence of the at least one bacterial microorganism.

35. The method of claim 33 wherein:

the step of selecting comprises selecting at least one isolated bacterial microorganism characterized by an ability, when cultured in the rhizosphere of the plant in an environment containing cadmium, to increase availability of the cadmium to the plant sufficiently so that the plant removes at least about 1.3 times as much cadmium from the environment as it would in the absence of the at least one bacterial microorganism;

the step of providing comprises providing a crop plant that is capable of accumulating an amount of cadmium; and the step of introducing comprises introducing into the rhizosphere of the crop plant at least one isolated bacterial microorganism characterized by an ability, when cultured in the rhizosphere of the plant in an environment containing cadmium, to increase availability of the cadmium to the plant sufficiently so that the plant removes at least about 1.3 times as much cadmium from the environment as it would in the absence of the at least one bacterial microorganism.

36. The method of claim 33 wherein:

the step of selecting comprises selecting at least one isolated bacterial microorganism characterized by an ability, when cultured in the rhizosphere of the plant in an environment containing lead, to increase availibility of the lead to the plant sufficiently so that the plant removes at least about 1.6 times as much lead from the environment as it would in the absence of the at least one bacterial microorganism;

the step of providing comprises providing a crop plant that is capable of accumulating an amount of lead; and the step of introducing comprises introducing into the rhizosphere of the crop plant at least one isolated bacterial microorganism characterized by an ability, when cultured in the rhizosphere of the plant in an environment containing lead, to increase availability of the lead to the plant sufficiently so that the plant removes at least about 1.6 times as much lead from the environment as it would in the absence of the at least one bacterial microorganism.

37. The method of claim 32 wherein the step of providing comprises providing a crop plant that is capable of accumulating the non-essential metal into its shoots.

38. The method of claim 32 wherein the step of selecting comprises selecting at least one bacterial microorganism that is capable of survival when growing under conditions of selection pressure, the selection pressure comprising exposure to increasingly high concentrations of the at least one non-essential metal; and wherein introducing comprises introducing into the plant rhizosphere at least one bacterial microorganism that has been selected based on its survival when growing under conditions of selection pressure, the selection pressure comprising exposure to increasingly high concentrations of the at least one non-essential metal.

39. The method of claim 38 wherein the step of introducing comprises:

providing at least one bacterial microorganism isolated from an environment containing the at least one non-essential metal; and subjecting the at least one isolated at least one bacterial microorganism to the selection pressure.

40. The method of claim 14, wherein the step of introducing comprises introducing the at least one bacterial microorganism into the rhizosphere of a common sunflower.

* * * * *